United States Patent [19]

Elliott et al.

[11] Patent Number: 4,696,944
[45] Date of Patent: Sep. 29, 1987

[54] PESTICIDAL CYCLOPROPANE CARBOXYLIC ACID ESTERS, THEIR COMPOSITIONS AND USE

[75] Inventors: Michael Elliott, Stevenage; Norman F. Janes, Luton; Bhupinder P. S. Khambay, Harrow Weald, all of England

[73] Assignee: National Research Development Corporation, United Kingdom

[21] Appl. No.: 711,812

[22] Filed: Mar. 14, 1985

[30] Foreign Application Priority Data

Mar. 15, 1984 [GB] United Kingdom ............... 8406731

[51] Int. Cl.⁴ .................. A01N 53/00; C07C 69/743; C07C 131/08
[52] U.S. Cl. .................................... 514/531; 560/124; 560/43; 560/102; 560/104; 560/106; 549/65; 564/256; 568/330; 568/379
[58] Field of Search .................. 560/124, 43, 102, 104, 560/106, 127; 514/531; 549/65

[56] References Cited

U.S. PATENT DOCUMENTS

| | | | |
|---|---|---|---|
| 3,636,059 | 1/1972 | Matsui et al. | 560/124 |
| 4,024,163 | 5/1977 | Eliott et al. | 514/531 |
| 4,304,733 | 12/1981 | Martel et al. | 560/124 |
| 4,356,187 | 10/1982 | Martel et al. | 560/124 |

OTHER PUBLICATIONS

Elliott, M., *J. Sci. Food Agric.*, vol. 5 (Nov. 1954), pp. 505-514, "Allethrin".

Clark, N. G., *Modern Organic Chemistry* (1964), Oxford University Press, p. 185.
*Chemical Abstracts*, vol. 100 (1984), p. 2132GS.

*Primary Examiner*—Paul J. Killos
*Assistant Examiner*—L. Hendriksen
*Attorney, Agent, or Firm*—Jacobs & Jacobs

[57] ABSTRACT

A compound of formula I

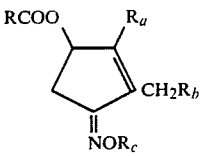

in which formula:

$R_a$ represents hydrogen or a $C_1$-$C_6$ alkyl group, and $R_c$ represents a $C_1$-$C_6$ alkyl group;

$R_b$ represents a phenyl group, optionally substituted by a $C_1$-$C_6$ alkyl group or halogen, a group of formula —CH=$CR_dR_e$ in which $R_d$ and $R_e$, which may be identical or different represent hydrogen or $C_1$-$C_6$ alkyl groups or a group of formula —CH=$NOR_f$ in which $R_f$ represents hydrogen or a $C_1$-$C_6$ alkyl group and RCOO represents a residue of an acid $RCO_2H$, which acid, or an ester-forming derivative of which acid, on reaction with α-cyano-3-phenoxybenzyl alcohol or an ester forming derivative thereof, gives rise to an α-cyano-3-phenoxybenzyl ester having pesticidal properties.

17 Claims, No Drawings

PESTICIDAL CYCLOPROPANE CARBOXYLIC ACID ESTERS, THEIR COMPOSITIONS AND USE

This invention relates to pesticides and in particular to pesticidal compounds, the preparation of such compounds, intermediates for use in their preparation, compositions containing such compounds and the use of such compounds and compositions to control pests, for example pests present in soil.

Accordingly the present invention comprises a compound of the formula I

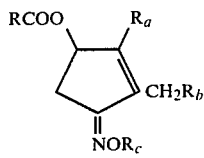

in which formula:

$R_a$ represents hydrogen or a $C_1$–$C_6$ alkyl group, and $R_c$ represents a $C_1$–$C_6$ alkyl group;

$R_b$ represents a phenyl group, optionally substituted by a $C_1$–$C_6$ alkyl group or halogen, a group of formula —CH=$CR_dR_e$ in which $R_d$ and $R_e$, which may be identical or different represent hydrogen or $C_1$–$C_6$ alkyl groups or a group of formula —CH=$NOR_f$ in which $R_f$ represents hydrogen or a $C_1$–$C_6$ alkyl group and RCOO represents a residue of an acid $RCO_2H$, which acid, or an ester-forming derivative of which acid, on reaction with α-cyano-3-phenoxybenzyl alcohol or an ester forming derivative thereof, gives rise to an α-cyano-3-phenoxybenzyl ester having pesticidal properties.

Although the acid residue RCOO may derive from a wide variety of acids as hereinafter described, it is preferred that the acid residue is of a cyclopropane carboxylic acid such as chrysanthemic acid or a 2,2-dimethyl-3-(dihalovinyl)cyclopropane carboxylic acid, 2,2-dimethyl-3-(dibromovinyl)cyclopropane carboxylic acid, especially when in the (IR,cis) form, being of especial interest.

When the group $R_b$ represents —CH=$NOR_f$, $R_f$ is preferably a $C_1$–$C_6$ alkyl group and when $R_b$ represents —CH=$CR_dR_e$, $R_d$ and $R_e$ usually represent hydrogen. It is generally preferred, however, that $R_b$ represents a phenyl group, which is typically unsubstituted. $R_a$ and $R_c$ are usually methyl groups and the configuration at the carbon atom carrying RCOO— may be R or S, although S is preferred.

Esters I may be prepared by reaction of an acid $RCO_2H$ or an esterifiable thereof with an intermediate of formula II

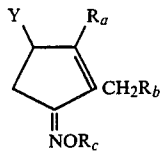

in which formula Y represents a hydroxyl group, an esterifiable derivative thereof or halogen e.g. bromine.

Intermediates of formula II are also included in a further aspect of the present invention.

It is particularly preferable that when Y represents halogen the intermediate II is reacted with a metal salt, particularly a silver or alkali metal salt of the acid $RCO_2H$.

Intermediates II in which Y represents a hydroxyl group or an esterifiable derivative thereof may be produced from compounds IIA by reaction thereof with an acid salt of the compound $R_cONH_2$ e.g. $R_cONH_2HCl$, suitably under basic conditions and typically in a polar solvent.

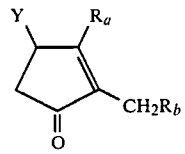

Intermediates II in which Y represents halogen may be produced from compounds IIB, by treatment thereof with a halogenating agent such as a N-halosuccinimide e.g. N-bromosuccimide.

Compounds IIA in which Y represents halogeun may also be produced by treatment of the ketone IIC.

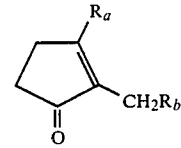

with a halogenating agent such as N-bromosuccinimide following which if the corresponding alcohol is required (IIA, Y=OH) the bromine may be replaced by an acetyl group, conveniently by reaction of IIA (Y=Br) with silver acetate and the acetyl derivative hydrolysed.

In an alternative procedure for the production of esters I, the acid $RCO_2H$ or an esterifiable derivative thereof is reacted with compound IIA in which Y represents a hydroxyl group, an esterifiable derivative thereof or halogen and the free carbonyl group in the ester thus produced is converted into the corresponding alkyl oxime usually by reaction with an acid salt of $R_cONH_2$ e.g. $R_cONH_2HCl$.

In the compounds of formula I, R represents the residue of a carboxylic acid RCOOH which is an acid known to be capable of forming pesticidal compounds when esterified with α-cyano-3-phenoxybenzyl alcohol. There are a large number of carboxylic acids that are known to form pesticidal compounds of this type and these carboxylic acids fall, for the most part, into two clearly defined groups. The first group is the cyclopropane carboxylic acids which are the compounds where R is a group of the formula:

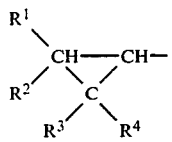

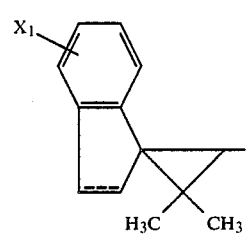

in formula III $R^3$ and $R^4$ will normally be an alkyl group, usually the same alkyl group, containing 1 to 4 carbon atoms and, as is well known in the art, dimethyl substitution normally gives high activity.

$R^2$ in formula III will normally be hydrogen or an alkyl group containing 1 to 4 carbon atoms and here the experience of the art indicates that $R^2$ will usually be hydrogen for maximum activity except in those compounds where $R^1$ is also an alkyl group, in which case $R^2$ preferably is an alkyl group, $R^1$, $R^2$, $R^3$ and $R^4$ all conveniently being the same alkyl group, e.g. methyl.

In formula III $R^1$ can be hydrogen or a substituted or unsubstituted acyclic or carbocyclic group. When $R^1$ is an unsubstituted hydrocarbyl group, it can be a straight chain or branched saturated or unsaturated acyclic or carbocyclic group such as an alkyl group, an alkenyl or alkadienyl group or a cycloalkyl, cycloalkylalkyl or cycloalkylalkenyl group. These hydrocarbyl groups preferably contain up to 10, particularly up to 6 carbon atoms.

When group $R^1$ is substituted, it is preferably one of the hydrocarbyl groups mentioned above which is substituted by one or more halogeno groups which may be fluorine, chlorine or bromine or by an alkoxy or oximino group or alkoxycarbonyl group, as in a group $R^1$ of particular interest of formula $-CH=CHCO_2R_x$ wherein $R_x$ represents an alkyl group typically containing 1 to 4 carbon atoms. When the substituents are two or more halogeno substituents, the halogeno substituents need not necessarily be the same halogen while when alkoxy groups are present, these preferably contain up to 4 carbom atoms and will normally be methoxy groups.

One particularly valuable structure for the group $R^1$ is of formula IV

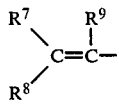

where $R^7$ and $R^8$, which may be the same or different, are each an alkyl group containing 1 to 4 carbon atoms, a trifluoromethyl group or a halogeno group, which may be the same or different and are preferably fluorine, chlorine or bromine. One of $R^7$ and $R^8$ may also represent hydrogen or a phenyl or substituted phenyl group. Alternatively, $R^7$ and $R^8$ may together form a straight or branched substituted or unsubstituted saturated or unsaturated divalent hydrocarbon chain which may be substituted by one or more hetero atoms e.g. O, N or S, so that $R^7$ and $R^8$ together with the carbon atom to which they are attached form a carbocyclic or heterocyclic ring which will preferably contain 5 to 7 ring atoms, optionally 1 or 2 carbon-to-carbon double bonds and optionally one or more alkyl ($C_1$-$C_4$) or halogeno substituents on the cycloaliphatic ring. Other compounds of interest are those in which R is a group of the structure where the dotted line represents an optional double bond and $X_1$ represents H or halogen such as chlorine.

Specific cyclopropane carboxylic acids from which the compounds I of the present invention may be structurally derived include the following:

Chrysanthemic acid including particularly (1R)-trans chrysanthemic acid;

Pyrethric acid;

Dimethylcyclopropane carboxylic acid;

Trimethylcyclopropane carboxylic acid;

Tetramethylcyclopropane carboxylic acid;

2,2-Dimethyl-3-(cyclopentylidenemethyl)cyclopropane carboxylic acid;

2,2-Dimethyl-3-(2,2-dibromovinyl)cyclopropane carboxylic acid; particularly the (1R)-cis isomer thereof;

2,2-Dimethyl-3-(2,2-dichlorovinyl)cyclopropane carboxylic acid; particularly the (1R)-cis isomer thereof;

2,2-Dimethyl-3-(1,2,2,2-tetrabromoethyl)cyclopropane carboxylic acid;

2,2-Dimethyl-3-(1,2-dibromo-2,2-dichloroethyl)cyclopropane carboxylic acid;

2,2-Dimethyl-3-(2-chloro-3,3,3-trifluoropropenyl)cyclopropane carboxylic acid;

2,2-Dimethyl-3-(tetrahydro-2-oxo-thien-3-ylidenemethyl)cyclopropane carboxylic acid.

The second major class of carboxylic acids from which the esters of formula I may be structurally derived are the α-substituted aryl acetic acid esters. In these compounds R in formula I will normally be of the structure

wherein Ar represents a divalent aryl residue, $R^5$ represents a saturated or unsaturated straight chain or branched acyclic or cyclic hydrocarbon residue and $R^6$ represents hydrogen or one or more alkyl, alkoxy (including substituted alkoxy such as $OCF_3$ and $OCHF_2$) or halogeno substituents.

Ar will normally be an aryl residue based on a benzene ring although other aryl residues, e.g. polynuclear residues are also of interest. $R^5$ will normally be a saturated straight or branched chain hydrocarbon group particularly an alkyl group containing up to 8 carbon atoms and it is often desirable that this alkyl group should contain at least one secondary carbon atom particularly when that secondary carbon atom is directly bonded to the carbon atom directly bonded to the $R^6$ substituted aryl group. Thus $R^5$ is preferably an isopropyl group or a secondary butyl group. $R^5$ can also be a cycloaliphatic residue, again preferably containing a secondary carbon atom located immediately adjacent to the carbon atom carrying the $R^6$ substituted phenyl group, e.g. $R^5$ may be a cyclopropyl group or an alkyl substituted cyclopropyl group. $R^5$ can also be a cycloalkylalkyl group.

$R^6$ is preferably one or more halogeno or halogen-containing substituents, e.g. F, Cl, Br or $OCHF_2$ or $OCF_3$ and, when more than one halogeno or halogen-containing substituent is present, they will normally be but are not necessarily the same halogen. When $R^6$ is an alkyl or alkoxy group, these preferably contain up to 4 carbon atoms and again, when more than one such group is present, they need not necesssarily be the same groups. When only one substituent $R^6$ is present, it is preferably present in the para-position. When more than one $R^6$ substituent is present, the para-position is preferably substituted together with one or more of the ortho- and meta-positions.

Another class of carboxylic acids from which the esters of the present invention may be structurally derived are α-substituted arylamino acetic acids of the type

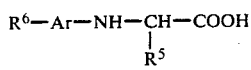

where $R^5$, $R^6$ and aryl are as defined above.

Specific-substituted phenyl acetic acids from which esters of the formula I may be structurally derived include:
α-Isopropyl-p-chlorophenyl acetic acid;
α-Cyclopropyl-p-chlorophenyl acetic acid;
α-Cyclopropyl-p-methylphenyl acetic acid;
α-Isopropyl-p-(difluoromethoxy)-phenyl acetic acid;
α-Isopropyl-(2-chloro-4-trifluoromethyl anilino)acetic acid.

The compounds of the invention exhibit optical isomerism in that the carbon atom bearing the substituent D can exist in the R or S configuration and the present invention includes compounds in which the configuration is substantially completely R or in which the configuration is substantially completely S or mixtures thereof.

Compounds of the invention in which R represents a substituted cyclopropane residue of formula III can exist in the form of both geometrical and optical isomers. This is because of the unsymmetrical substitution at $C_1$ and $C_3$ of the cyclopropane ring. Compounds of the present invention include those isomers in which the hydrogen atoms at $C_1$ and $C_3$ of the cyclopropane ring are substantially completely in the cis configuration or substantially completely in the trans configuration or mixtures thereof. The present invention also includes compounds in which the configuration at $C_1$ is substantially completely R or substantially completely S and mixtures thereof. In the compounds of the invention in which R represents a group of formula III, the optical configuration at $C_1$ and $C_3$ cannot vary independently of the geometrical configuration of the hydrogen atoms at $C_1$ and $C_3$ of the cyclopropane ring. The effect of this is that the configuration of the cyclopropane ring can be defined uniquely by specifying the optical configuration at $C_1$ and the geometrical configuration of the hydrogen atoms at $C_1$ and $C_3$ and, for definition purposes, we have adopted nomenclature of the form (1R)-cis, (1R)-trans etc. it being unnecessary to specify the optical configuration at $C_3$ which is fixed once the other two variables are defined. Adopting this nomenclature avoids the confusion which can arise by having to designate either R or S to the same optical configuration at $C_3$ depending upon the nature of the substituents on the cyclopropane ring and even those on the side chain.

When R is a group of formula III in which $R^1$ is a group of formula IV in which the substitution about the ethylenic bond is asymmetrical, that is to say $R^7 \neq R^8$ then the configuration of this part of the molecule can be substantially completely in the E form or substantially completely in the Z form or a mixture thereof.

When R is a group of formula V, the carbon atom to which $R^5$ is bonded can exist substantially completely in the S configuration or substantially completely in the R configuration or can be a mixture of the two forms.

The compounds of the present invention can be in the form of single isomers but, having regard to the fact that the compounds have at least one and frequently more than one centre of asymmetry, the compounds of the invention will normally be in the form of isomer mixtures although these isomer mixtures can be optically active and/or substantially completely in one geometric form.

When, as hereinbefore described, the compounds of the present invention are prepared by an esterification involving the reaction of an alcohol of formula II or an esterifiable derivative thereof with a carboxylic acid of formula RCOOH or an esterifiable derivative thereof, it is usually convenient in practice to react an alcohol of formula II with an acyl chloride of formula RCOCl or to esterify the carboxylic acid with the alcohol in the presence of dicyclohexyl carbodi-imide and a catalyst. Alternatively, the esters of the invention can be prepared by transesterification by reacting a $C_1$–$C_6$ alkyl ester of the carboxylic acid with an alcohol of formula II in the presence of a basic transesterification catalyst. This method is not usually satisfactory where the molecule contains another base-sensitive residue, e.g. where the carboxylic acid is pyrethric acid.

One or more of the pesticidal esters of formula I can be formulated with an inert carrier or diluent to give pesticidal compositions and such compositions form a further aspect of the present invention. These compositions can be in the form of dusts and granular solids, wettable powders, mosquito coils and other solid preparations, or as emulsions, emulsifiable concentrates, sprays and aerosols and other liquid preparations after the addition of the appropriate solvents, diluents and surface-active agents.

Compositions formulated in a manner suitable for controlling soil pests typically by treatment of the soil are of especial interest. For this purpose compositions containing compounds I hereinbefore described are particularly suitable as they generally have lower molecular weights than many previously described pyrethroids, and it is envisaged that their relatively high vapour pressures allow them to diffuse through the soil.

The pesticidal compositions of the invention will normally contain from 0.001 to 25% by weight of the compound of formula I but the compositions can contain higher concentrations of active ingredient of formula I e.g. up to 95% for compositions to be sold as concentrates for dilution before use by the ultimate user.

The compositions of the invention can include diluents such as hydrocarbon oils, e.g. xylene or other petroleum fractions, water, anionic, cationic or non-ionic surface-active agents, anti-oxidants and other stabilisers as well as perfumes and colouring matters. These inert ingredients may be of the type and in proportions such as are conventionally used in pesticidal compositions containing pyrethroid-like compounds.

In addition to these inactive ingredients, the compositions of the present invention may contain one or more further active ingredients which may be other pesticidal compounds of the pyrethroid type or of other types and the composition may also include synergists of the type known to be capable of synergising the activity of natural pyrethrin and pyrethroid-like insecticides. Synergists of this type include piperonyl butoxide, tropital and sesamex.

The compounds of formula I can be used to control pest infestation in the domestic, horticultural or agricultural or medical, including veterinary, areas. The compounds or compositions of the invention can be used to combat pest infestation by treating pests or surfaces or environments susceptible to pest infestation with effective amounts of the active compounds of formula I or of compositions containing them. For example, they may be used in a domestic environment for spraying rooms to combat infestation with houseflies or other insects, they can be used for treatment of stored dry crops or cereals to combat infestation by insects or other pests, they can be used to spray growing crops, e.g. cotton or rice to combat infestation by common pests and they can be used in a medical or veterinary field, e.g. as a cattle spray to prevent or treat infestation by insects or other pests.

Although, as hereinbefore indicated, they are of particular interest for the disinfestation of soil to control pests such as the onionfly, Delia antiqua, the compounds may find application in the control of a wide variety of pests including:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera spec.;* from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea madarae, Blattela germanica, Acheta domesticus,* Gryllotalpa spp., *Locusta migratoria migratorioides, Melanoplus differentialis* and *Schistocera gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Demalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolius* and Triatoma spp.;

from the order of the Hemoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aondiiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Peieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolntha, Amphimallon solstitialis* and *Costeyltra zealandica;* from the order of the Hymenoptera, for example Diprion spp., Hoplacampa spp., Lasius spp., *Monomorium pharaonis* and Vespa spp., from the order of the Diptera, for example Aedes spp., Anopheles spp., Culex spp., *Drosophilia melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus,* Oscinella frit, Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The invention is illustrated by the following Examples.

Temperatures are in ° C.

EXAMPLE 1

Methyloxime of allethrolone

A mixture of allethrolone (4 g), methoxylamine hydrochloride (3.3 g), pyridine (4 g), THF (50 ml) and water (8 ml) is refluxed for 2 hours. Most of the solvent is then removed under reduced pressure. Dilute HCl is added and the mixture extracted with Et₂O (×3). The extracts are combined, dried and the solvent removed under reduced pressure. Yield 4.26 g $n_D$ 1.5192.

EXAMPLE 2

(IR)-trans-chrysanthemate of allethrolone methyl oxime

The product from Example 1 is esterified by following a known procedure to yield the ester, $n_D^{20}$ 1.5122.

EXAMPLE 3

(IR)-cis-3-(2,2-dibromovinyl)-2,2-dimethylcyclopropane carboxylic ester of allethrone methyl oxime The product from Example 1 is esterified by following a known procedure to yield the ester $n_O^{20}$ 1.5452.

EXAMPLE 4

Methyl oxime of 2-benzyl-4-hydroxycyclo-pent-2-en-1-one

A. 2-benzyl-4-hydroxycyclopent-2-en-1-one

A mixture of 2-benzylcyclopent-2-en-1-one and N-bromosuccinimide in dry carbon tetrachloride (150 ml) is refluxed for 1 hour, cooled and filtered. The filtrate is concentrated under reduced pressure to approx. 100 ml, and mixed with a stirred suspension of silver acetate (5 g) in acetic acid (150 ml). The resulting mixture is heated to 50° C. for 30 minutes and then stirred at room temperature overnight. The mixture is filtered, poured onto H₂O (50 ml) and extracted with methylene chloride (150 ml×3). The combined extracts are washed with water ag. sodium bicarbonate, ag. sodium chloride, dried and concentrated under reduced pressure. (b.pt. is 128°-132° at 0.05 mmHg). The crude acetate is added to a solution of KOH (1.1 g) in 10% aqueous MeOH (100 ml) and stirred at room temperature for 40 minutes, poured onto dil.HCl and extracted with Et₂₀ (×3). The combined extracts are washed with water dried, concentrated under reduced pressure and finally distilled. The ketone has b.pt 150°-154° C. at 0.04 mmHg and $n_D$ 1.5562.

B. Methyloxime of 2-benzyl-4-hydroxycyclopent-2-en-1-one

The hetone from procedure A (0.2 g) is mixed with pyridine (0.25 g), methoxyamine hydrochloride (0.25 g), dioxane (3 ml) and water (0.5 ml). The mixture is refluxed for 2 hours and then poured onto water and extracted with methylene chloride (3 times). The combined extracts are washed with water, dried and the solvent removed by evaporation.. Purification is effected by thin layer chromatography, eluting with 50% diethylether/Petroleum ether (60/80), the yield being 0.15 g.

EXAMPLE 5

(IR)-cis-3-(2,2-dibromovinyl)-2,2-dimethylcyclopropane carboxylic ester of 2-benzyl-4-hydroxycyclopent-2-en-1-one methyloxime The product from Example 4 is esterified by a known procedure to yield the ester, $n_D^{20}$ 1.5690.

The pesticidal activity is assessed against houseflies and mustard beetles by using the following techniques:

Houseflies (musca domestica)

Female flies are treated on the thorax with one microliter drop of insecticide dissolved in acetone. Two replicates of 15 flies are used at each dose rate and 6 dose rates are used per compound under test. After treatment, the flies are maintained at a temperature of 20°±1° and kill is assessed 24 and 48 hours after treatment. LD₅₀ values are calculated in micrograms of insecticide per fly and relative toxicities are calculated from the inverse ratios of the LD₅₀ values (see Sawicki et al, Bulletin of the World Health Organisation, 35, 893 (1966) and Sawicki et al, Entomologia and Exp. Appli. 10, 253, (1967)).

Mustard Beetles (Phaedon cochleariae Fab)

Acetone solutions of the test compound are applied ventrally to adult mustard beetles using a micro drop applicator. The treated insects are maintained for 48 hours after which time kill is assessed. Two replicates of 40 to 50 mustard beetles are used at each dose level and 5 dose levels are used for each compound. Again, LD₅₀ values are calculated and relative potencies are calculated from the inverse ratios of LD₅₀ (see Elliott et al, J. Sci. Food Agric. 20, 561, (1969)).

Relative potencies are calculated by comparison with 5-benzyl-3-furylmethyl (IR)-trans-chrysanthemate (Bioresmethrin) which is one of the more toxic chrysanthemate esters known to house flies and mustard beetles, its toxicity being about 24 times that of allethrin to houseflies and 65 times that of allethrin to mustard beetles. Bioassay results are set forth in the Table.

TABLE

Compounds 1
$C_R$ = (IR)—trans chrysanthemyl
$B_R$ = (IR)—cis-3-(2,2-dibromovinyl)-2,2-dimethyl cyclopropane carboxyl

| Example No. | $R_a$ | $R_b$ | $R_c$ | $n_D^{20}$ | R | Relative Potencies (Bioresmethrin = 100) HF | MB |
|---|---|---|---|---|---|---|---|
| 2 | CH₃ | —CH=CH₂ | CH₃ | 1.5122 | $C_R$ | 11 | 1.8 |
| 3 | CH₃ | —CH=CH₂ | CH₃ | 1.5452 | $B_r$ | 10 | 3.8 |
| 5 | H | Ph | CH₃ | 1.5690 | $B_R$ | 52 | 12 |
| 6 | CH₃ | —CH=NOCH₃ | CH₃ | 1.5060 | $C_R$ | 1.2 | ca. 0.5 |
| 7 | CH₃ | —CH=NOCH₃ | CH₃ | 1.5388 | $B_R$ | 15 | 3.5 |

We claim:
1. A compound of the formula I

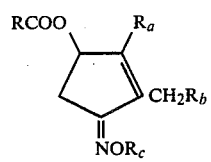

in which formula:
$R_a$ is hydrogen or alkyl of 1 to 6 carbon atoms, and $R_c$ is alkyl of 1 to 6 carbon atoms:
$R_b$ is phenyl unsubstituted or substituted by alkyl of 1 to 6 carbon atoms or halogen, a group of the formula —CH=CR$_d$R$_e$ in which R$_d$ and R$_e$ are identical or different and each is hydrogen or alkyl or a group of the formula —CH=NOR$_f$ in which R$_f$ is hydrogen or alkyl of 1 to 6 carbon atoms and RCOO is a residue of an acid RCO$_2$H selected from the group consisting of chrysanthemic acid and 2,2-dimethyl-3-(dihalovinyl)cyclopropane carboxylic acid.

2. A compound according to claim 1, in which the acid residue is of said cyclopropane carboxylic acid.

3. A compound according to claim 2, in which the acid residue is of [IR,cis]2,2-dimethyl-3-(2,2-dibromovinyl)cyclopropane carboxylic acid.

4. A compound according to claim 1, in which R$_b$ is phenyl unsubstituted or substituted by alkyl of 1 to 6 carbon atoms or halogen.

5. A compound according to claim 1, in which R$_a$ is hydrogen, R$_b$ is phenyl, R$_c$ is methyl and R is [IR,cis]-2,2-dimethyl-3-(2,2-dibromovinyl)-cyclopropyl.

6. A pesticidal composition useful for controlling pest infestation which comprises a pestically effective amount of a compound of the formula I:

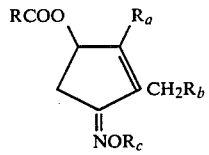

wherein:
R$_a$ is hydrogen or alkyl of 1 to 6 carbon atoms, and R$_c$ is alkyl of 1 to 6 carbon atoms:
R$_b$ is phenyl unsubstituted or substituted by alkyl of 1 to 6 carbon atoms or halogen, a group of the formula —CH=CR$_d$R$_e$ in which R$_d$ and R$_e$ are identical or different and each is hydrogen or alkyl or a group of the formula —CH=NOR$_f$ in which R$_f$ is hydrogen or alkyl of 1 to 6 carbon atoms and RCOO is a residue of an acid RCO$_2$H selected from the group consisting of chrysanthemic acid and 2,2-dimethyl-3-(dihalovinyl)cyclopropane carboxylic acid, in combination with a suitable carrier.

7. A composition according to claim 6 wherein the acid residue is of said cyclopropane carboxylic acid.

8. A composition according to claim 6 wherein the acid residue is of [IR,cis]2,2-dimethyl-3-(2,2-dibromovinyl)cyclopropane carboxyl acid.

9. A composition according to claim 6 wherein R$_b$ is phenyl unsubstituted or substituted by alkyl of 1 to 6 carbon atoms or halogen.

10. A composition according to claim 6 wherein R$_a$ is hydrogen, R$_b$ is phenyl, R$_c$ is methyl and R is [IR,cis]-2,2-dimethyl-3-(2,2-dibromovinyl)-cyclopropyl.

11. A composition according to claim 6 in the form of a dust, granular solid, wettable powder, mozquito coil, emulsion emulsifiable concentrate, spray or aerosol.

12. A method of combatting pest infestation which comprises treating pets or surfaces or environments susceptible to pest infestation with a pesticidally effective amount of a compound of the formula I:

R$_a$ is hydrogen or alkyl of 1 to 6 carbon atoms, and R$_c$ is alkyl of 1 to 6 carbon atoms:
R$_b$ is phenyl unsubstituted or substituted by alkyl of 1 to 6 carbon atoms or halogen, a group of the formula —CH=CR$_d$R$_e$ in which R$_d$ and R$_e$ are identical or different and each is hydrogen or alkyl or a group of the formula —CH=NOR$_f$ in which R$_f$ is hydrogen or alkyl of 1 to 6 carbon atoms and RCOO is a residue of an acid RCO$_2$H selected from the group consisting of chrysanthemic acid and 2,2-dimethyl-3-(dihalovinyl)cyclopropane carboxylic acid, in combination with a suitable carrier.

13. A method according to claim 12 wherein the acid residue is of said cyclopropane carboxylic acid.

14. A method according to claim 12 wherein the acid residue is of [IR,cis]2,2-dimethyl-3-(2,2-dibromovinyl)-cyclopropane carboxyl acid.

15. A method according to claim 12 wherein R$_b$ is phenyl unsubstituted or substituted by alkyl of 1 to 6 carbon atoms or halogen.

16. A method according to claim 12 wherein R$_a$ is hydrogen, R$_b$ is phenyl, R$_c$ is methyl and R is [IR,cis]-2,2-dimethyl-3-(2,2-dibromovinyl)-cyclopropyl.

17. A method according to claim 12 wherein the pesticide is in the form of a dust, granular solid, wettable powder, mozquito coil, emulsion emulsifiable concentrate, spray or aerosol.

* * * * *